US005714143A

United States Patent [19]
Blake et al.

[11] Patent Number: 5,714,143
[45] Date of Patent: Feb. 3, 1998

[54] USE OF MANGANESE SUPEROXIDE DISMUTASE (MN-SOD) FOR PREPARING PHARMACEUTICAL COMPOSITIONS FOR LOW-DOSE TREATMENT OF DISEASES

[75] Inventors: David R. Blake, Droitwich; Ewa J. Dowling, Chalfont St. Peter, both of Great Britain; Christian Lillie, Vienna; Andreas Zöphel, Neulengbach, both of Austria

[73] Assignee: Boehringer Ingelheim International GmbH, Germany

[21] Appl. No.: 118,264

[22] Filed: Sep. 9, 1993

[30] Foreign Application Priority Data

Sep. 9, 1992 [DE] Germany .................. 42 29 801.6

[51] Int. Cl.$^6$ .................................................. A61K 38/44
[52] U.S. Cl. ............................................................ 424/94.4
[58] Field of Search ................................................. 424/94.4

[56] References Cited

U.S. PATENT DOCUMENTS

| | | | |
|---|---|---|---|
| 5,116,616 | 5/1992 | Gonenne | 424/94.4 |
| 5,240,847 | 8/1993 | Heckl et al. | 435/189 |
| 5,246,847 | 9/1993 | Hartman et al. | 435/189 |
| 5,260,204 | 11/1993 | Heckl et al. | 435/189 |
| 5,264,211 | 11/1993 | Gonenne | 424/94.4 |
| 5,270,195 | 12/1993 | Hartman et al. | 435/189 |

FOREIGN PATENT DOCUMENTS

| | | |
|---|---|---|
| 0 284 105 | 9/1988 | European Pat. Off. . |
| 2 183 658 | 6/1987 | United Kingdom . |

OTHER PUBLICATIONS

Baret et al., "Pharmacokinetic and Anti–Inflammatory Properties in the rat of superoxide dismutases (Cu SODs and Mn SOD) From Various Species", *Biochem. Pharmacol.* 33: 2755–2760 (1984).

Block et al., "Prevention of Hyperoxic–Induced Depression of Pulmonary Serotonin Clearance by Pretreatment with Superoxide Dismutase", *Am. Rev. Resp. Dis.* 116: 441–447 (1977).

Del Villano et al., "Elevated Superoxide Dismutase in Black Alcoholics", *Science* 207:991–993 (Feb. 29, 1980).

Evans et al., "Oxidant–Mediated Lung Disease in Newborn Infants" *J. Free Rad. in Biol. & Med.* 2: 369–372 (1986).

Gannon et al., "Time–Dependent Inhibition of Oxygen Radical Induced Lung Injury", *Inflammation* 14: 509–522 (1990).

Giri et al., "The Effects of Paraquat and Superoxide Dismutase on Pulmonary Vascular Permeability and Edema in Mice", *Arch. Envir. Health* 36: 149–154 (1981).

Gorecki et al., "Recombinant Human Superoxide Dismutases:Production and Potential Therapeutical Uses", *Free Rad. Res. Comms.* 13: 401–410 (1991).

Ho et al., "Isolation and characterization of complementary DNAs encoding human manganese–containing superoxide dismutase", *Febs Letters* 229: 256–260 (Mar. 1988).

Johnson et al., "Superoxide Dismutase Prevents the Thrombin–Induced Increase in Lung Vascular Permeability: Role of superoxide in Mediating the Alterations in Lung Fluid Balance", *Circ. Res.* 59: 405–415 (Oct. 1986).

Kashimoto et al., "Protective Effects of Superoxide Dismutase Against Oxygen Toxicity in Rat's Heart Lung Preparation", *Jap. Circ. J.* 51: 1022–1026 (Sep. 1987).

Lee et al., "Studies on Superoxide Dismutase and Catalase Activities in Rats' Brains that were exposed to High $O_2$ Tension following Intratracheal Administration of Superoxide dismutase", *Chung–Ang. J. of Med.* 13: 341–351 (Sep. 1988).

Malaker, K. & Das, R.M., "The Effect of Superoxide Dismutase on the Pathogenesis of Radiation–Induced Pulmonary Damage in the Rat", *Pharmac. Ther.* 39: 327–330 (1988).

Malaker, K. & Das, R.M. "Effect of superoxide dismutase on early radiation injury of lungs in the rat" *Mol. & Cell. Biochem.* 84: 141–145 (1988).

McCord et al., "A Manganese–Containing Superoxide Dismutase From Human Liver", *Superoxide and Superoxide Dismutase (A.M. Michelson, J.M. McCord, I. Fridovich, eds.)* Academic Press, N.Y., 129–138 (1977).

McCord, J.M. & Roy, R.S. "The pathophysiology of superoxide: roles in inflammation and ischemia", *Can. J. Physiol. Pharmacol.* 60: 1346–1352 (1982).

Nimrod et al., "Recombinant Human Manganese Superoxide Dismutase (r–hMsSOD) is a potent anti–inflammatory agent", *Medical, Biochemical and Chemical Aspects of Free Radicals*, O. Hayaishi et al., eds. Elsevier Science Publshers, B.V. Amsterdam, pp. 743–746 (1989).

Oda et al., "Oxygen Radicals in Influenza–Induced Pathogenesis and Treatment with Pyran Polymer–Conjugated SOD", *Science* 244: 974–976 (May 26, 1989).

Omar, B.A., McCord, J.M., "The Cardioprotective Effect of Mn–Superoxide Dismutase is Lost at High Doses in the Postischemic Isolated Rabbit Heart", *Free Radical Biol. & Med.* 9: 473–478 (1990).

Omar, B.A., McCord, J.M., "Interstitial Equilibration of Superoxide Dismutase Correlates with its Protective Effect in the Isolated Rabbit Heart" *J. Mol. Cell. Cardiol.* 23: 149–159 (1991).

Padmanabhan et al., "Protection against Pulmonary Oxygen Toxicity in Rats by the Intratracheal Administration of Liposome–Encapsulated Superoxide Dismutase or Catalase", *Am. Rev. Resp. Dis.* 132:164–167 (1985).

Parizada et al., "Protective Effects of Human Recombinant MnSOD in Adjuvant Arthritis and Bleomycin–Induced Lung Fibrosis", *Free Rad. Res. Comms.* 15: 297–301 (1991).

(List continued on next page.)

*Primary Examiner*—Jean C. Witz
*Attorney, Agent, or Firm*—Sterne, Kessler, Goldstein & Fox P.L.L.C

[57] ABSTRACT

The present invention relates to the use of pharmaceutical preparations containing manganese superoxide dismutase in a low dose for treating diseases and conditions caused by free oxygen radicals.

7 Claims, 3 Drawing Sheets

OTHER PUBLICATIONS

Rosenfeld et al., "Prevention of Bronchopulmonary Dysplasia by Administration of Bovine Superoxide Dismutase in Preterm Infants with Respiratory Distress Syndrome", *J. Pediat.* 105: 781–785 (Nov. 1984).

Seo et al., (unverified English translation) "The Effect of Intratracheally Administered Free and Liposome Entrapped Superoxide Dismutase and Catalase on Experimentally exposed Hyperoxic Injury in Rat's Lung", *Chung-Ang J. of Med.* 12: (Jun. 1987).

Seo et al., (original document in English/Korean) "The Effect of Intratracheally Administered Free and Liposome Entrapped Superoxide Dismutase and Catalase on Experimentally exposed Hyperoxic Injury in Rat's Lung", *Chung-Ang J. of Med.* 12: 259–271 (Jun. 1987).

Shaffer et al., "Administration of bovine superoxide dismutase fails to prevent chronic pulmonary sequelae of neonatal oxygen exposure in the rat", *J. Pediatrics* 110: 942–946 (Jun. 1987).

Tanswell, A.K. & Freeman, B.A., "Daily Intraperitoneal Injections of Liposomes Containing Superoxide Dismutase (SOD) and Catalase (CAT) Protects Newborn Rats From the Lethal Effects of 100% Oxygen", *Ped. Res. Abstract* 1914: 479A (1986).

Turrens et al., "Protection against Oxygen Toxicity by Intravenous Injection of Liposome-entrapped Catalase and Superoxide Dismutase", *J. Clin. Invest.* 73: 87–95 (Jan. 1984).

Walther et al., "Prevention of Oxygen Toxicity with Superoxide Dismutase and Catalase in Premature Lambs", *J. Free Rad. in Biol. & Med.* 2: 289–293 (1986).

Wang et al., "Oxygen–Derived Free Radicals Induced Cellular Injury in Superior Mesenteric Artery Occlusion Shock", *Circ. Shock* 32: 31–41 (1990).

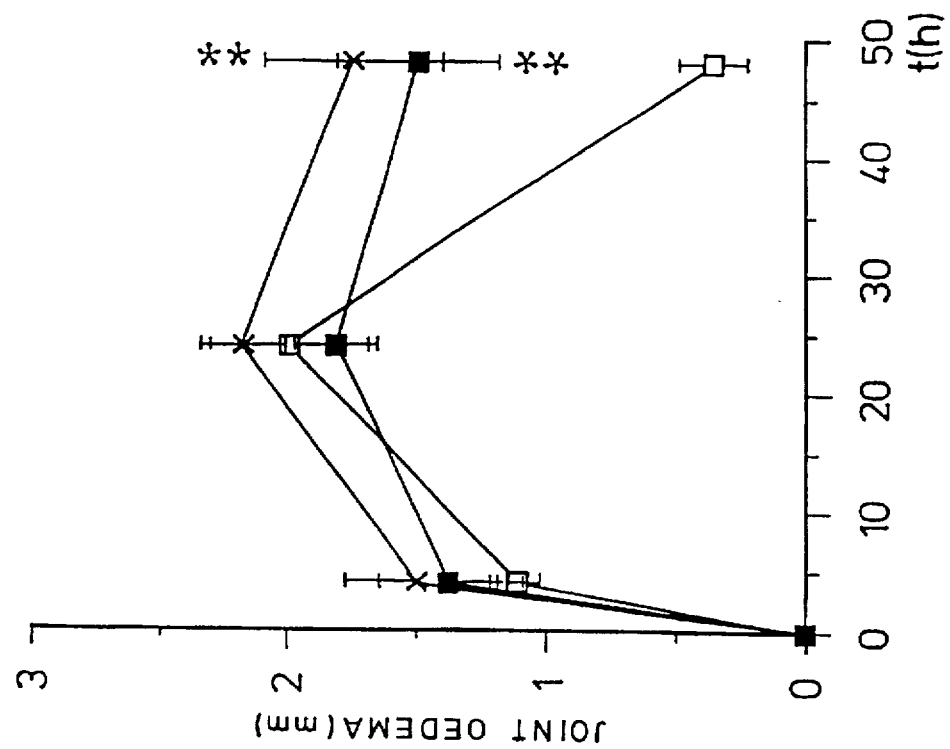
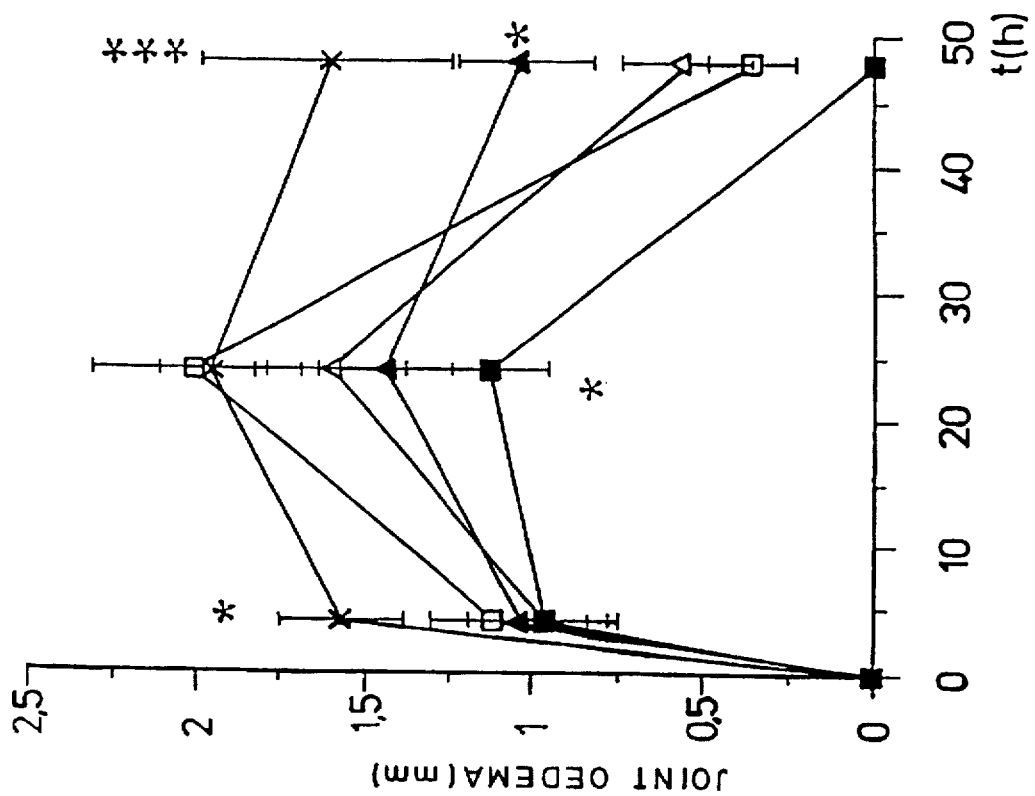

USE OF MANGANESE SUPEROXIDE DISMUTASE (MN-SOD) FOR PREPARING PHARMACEUTICAL COMPOSITIONS FOR LOW-DOSE TREATMENT OF DISEASES

FIELD OF THE INVENTION

The present invention is in the field of medicinal chemistry. The invention relates in particular to methods for treating or preventing inflammation caused by superoxide radicals by administration of low doses of manganese superoxide dismutase.

BACKGROUND OF THE INVENTION

It is known that, as a consequence of various biochemical processes in biological systems (e.g. Redox processes in the respiratory chain, oxidations in the cytoplasm), $O_2$. radicals are continuously formed which are highly cytotoxic and may lead to tissue damage. In pathological situations, e.g. in the course of rheumatic disorders, there may be degradation of collagen and synovial fluid by such radicals (Pasquier, C. et al., *Inflammation* 8:7–32 (1984)).

Eukaryotic cells contain primarily two forms of superoxide dismutases (SOD), one of which occurs predominantly in the cytosol (Cu/Zn-SOD) whilst the other occurs primarily in the mitochondria (Mn-SOD). In liver mitochondria it has been found that the Mn-SOD enzyme is located in the matrix enclosing the inner membrane, although Mn-SOD has also been detected in the cytosol of the liver cells (Mc Cord J. M., et al., In: *Superoxide and Superoxide Dismutases* (A. M. Michelson, J. M. Mc Cord, I. Fridovich, eds.) Academic Press, N.Y., 129–138 (1977)).

In prokaryotes, there is an Fe-SOD in addition to an Mn-SOD. Fe-SOD has also been detected in algae and protozoa and in some plant species (Bridges, S. M., Salin, M. L., *Plant Physiol.* 68:275–278 (1981)).

These highly active enzymes catalyze the disproportionation $O_2.^- + O_2.^- 2H^+ \rightarrow H_2O_2 + O_2$ and by this dismutation of the superoxide radicals prevent concentration thereof and hence any cell damage. Apart from the endoplasmic reticulum of the liver, the mitochondrial membranes are regarded as one of the most important sites of $O_2$ production in animal cells, so it is no wonder that mitochondria have their own special SOD (Mn-SOD).

The structural gene of a prokaryotic Mn-SOD (*E. coli*) has been cloned and the chromosomal sodA-gene has been located (Touati, D., *J. Bact.* 155:1078–1087 (1983)).

The 699 bp long nucleotide sequence of a mitochondrial yeast Mn-SOD has been clarified and the primary structure both of the precursor and of the mature protein have been derived therefrom—with molecular weights of 26123 Da for the precursor and 23059 Da for the mature protein (Marres, C. A. M., et al., *Eur. J. Biochem.* 147:153–161 (1985)). Thus, the Mn and Cu/Zn-SOD (MW=14893, EP-A-138111) differ significantly in their molecular weight.

The complete amino acid sequence of Mn-SOD from human liver has been published by Barra, and according to this the hMn-SOD is supposed to consist of 196 amino acids (Barra, D., et at., *J. Biol. Chem.* 259:12595–12601 (1984)). Human Cu/Zn-SOD from erythrocytes, on the other hand, consists of 153 amino acids (Jabusch, J. R., et al., *Biochemistry* 19:2310–2316 (1980)) and exhibits no sequence homologies to hMn-SOD (Barra, D., et al., see above).

Generally, the superoxide dismutases are credited with a protective function against certain inflammatory processes. In particular, a deficiency of Mn-SOD is thought to be significant in the development of rheumatoid arthritis (Pasquier, C., et at., see above). It is also assumed that SOD has a protective effect against alcohol-induced liver damage (Del Villano, B. C., et al., *Science* 207:991–993 (1980)). Furthermore, SOD is reported to protect ischemic tissues (McCord, J. M. & Roy, R. S., *Can. J. Physiol. Pharma* 60:1346–1352 (1982)) and to have a cardioprotective effect, in that the SOD exerts a protective effect on myocardial cells in hypoxia or in tissue damage caused by reperfusion (Omar, B. A., McCord, J. M., *J. Mol. Cell. Cardiol* 23:149–159 (1991)).

It is generally known that oxygen free radicals play a central part in all kinds of cell and tissue damage and are one of the main factors, particularly, in triggering inflammatory processes.

In accordance with this finding, attempts have been made to use SOD as a therapeutic agent particularly in diseases which involve inflammatory processes.

However, it has been found that either the quantities of Mn-SOD used, in the milligram range (mg/kg of body weight), had negative effects, which might result in exacerbation of the inflammatory process, or that the Mn-SOD had no effect whatsoever (Omar, B. A., McCord, J. M., *Free Radical Biol. Med.* 9:473–478 (1990); Baret, A. et al., *Biochem. Pharmacol.* 33:2755–2760 (1984)). Accordingly, it is proposed in EP-A 284 105 to use Mn-SOD in a preferred dosage of between 3 and 50 mg/kg of body weight to treat inflammatory diseases, or as described by Nimrod, A. et al., in: *Medical, Biochemical and Chemical Aspects of Free Radicals*, O. Hayaishi et al., eds. Elsevier Science Publishers, B. V. Amsterdam, pp. 743–746 (1989), a dosage range of 5 to 50 mg/kg of body weight being specified. It is known from publication by Gorecki, M., et al., *Free Rad. Res. Comms.* 12–13:401–410 (1991)), that Mn-SOD has a radio protective effect at a dose of 100 mg/kg i.v. and is supposed to be anti-inflammatory within a dosage range from 8 to 20 mg/kg i.v. or at 50 mg/kg s.c.

SUMMARY OF THE INVENTION

The present invention relates to the use of manganese superoxide dismutase (Mn-SOD) for preparing a pharmaceutical preparation for the therapeutic or prophylactic treatment of diseases or conditions which are caused, partly caused or triggered by oxygen free radicals, containing 1 to 200 μg of Mn-SOD, based on a daily dose of per kg of body weight in mammals, including humans. Preferably, the preparation contains 1 to 100 μg/kg of body weight of Mn-SOD. More preferably, the preparation contains 1 to 50 μg/kg of body weight of Mn-SOD.

The invention also relates to pharmaceutical preparations for treating tissue damage, in particular, for treating inflammatory processes and for treating tissues and organs after transplantation.

The invention also relates to the use of manganese superoxide dismutase (Mn-SOD) for preparing a pharmaceutical preparation for treating inflammatory diseases in joints, containing 1 to 20 μg of (Mn-SOD), based on the volume of a knee joint of 100 μl. More preferably, the preparation contains 1 to 10 μg of Mn-SOD. Most preferably, the preparation contains 1 to 5 μg of Mn-SOD.

The pharmaceutical preparation of the present invention may be formulated for systemic administration or based on sustained release forms.

The present invention also relates to pharmaceutical compositions in unit dosage form comprising, as active ingredient, Mn-SOD in association with one or more pharmaceutically acceptable carriers or excipients, wherein each unit dose contains less than 14 mg of Mn-SOD. Preferably, the unit dose contains less than 7 mg of Mn-SOD. More preferably, the unit dose contains less than 3.5 mg of Mn-SOD. Even more preferably, the unit dose contains less than 1.2 mg of Mn-SOD. Even more preferably, the unit dose contains less than 0.6 mg of Mn-SOD. Most preferably, the unit dose contains less than 0.3 mg of Mn-SOD.

Figure 1A:
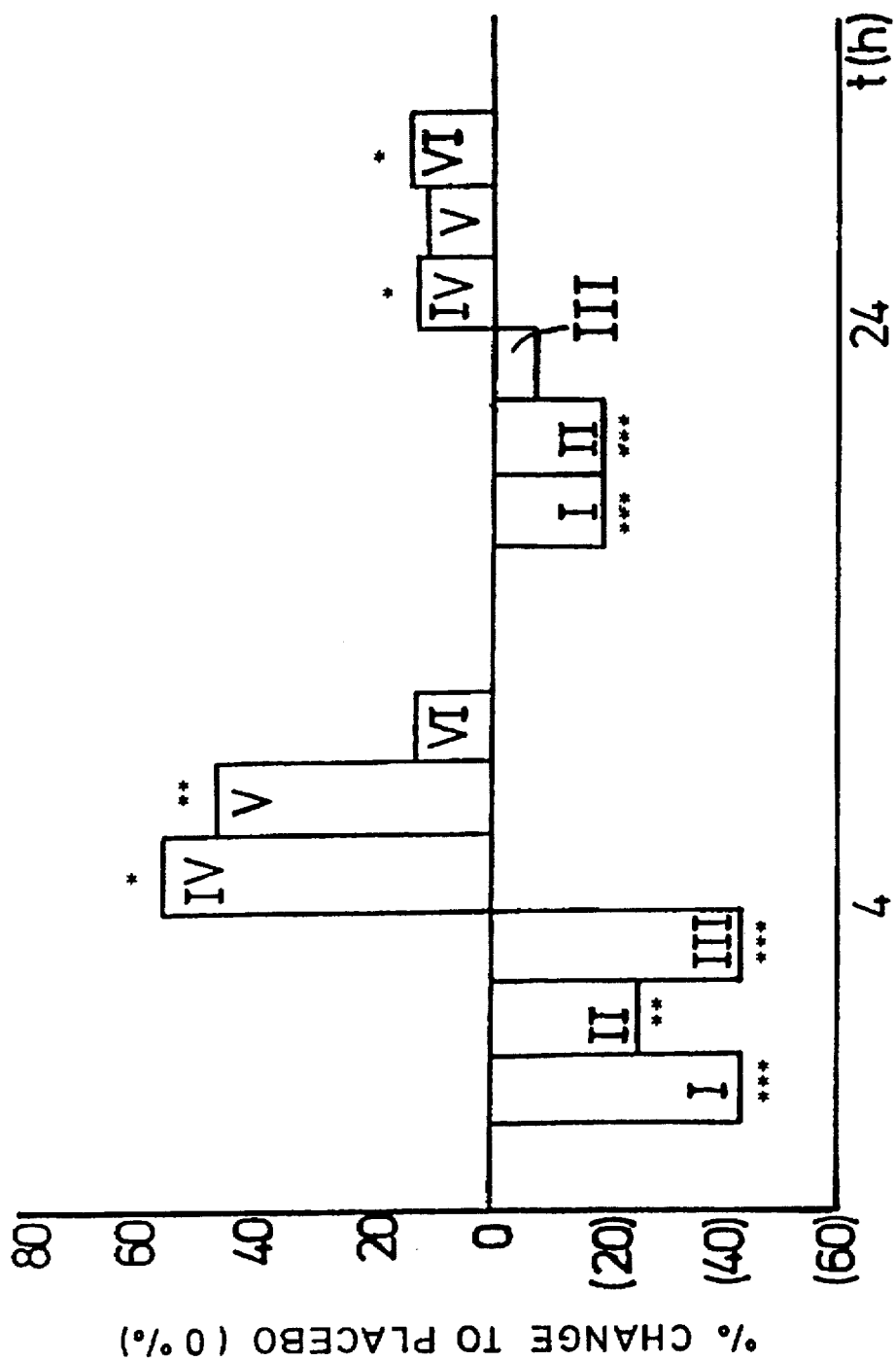
FIGS. 1a and 1b depict graphs showing the dosage reaction of (a) rh Mn-SOD and (b) Cu/Zn-SOD in oedemas in an FCA-mediated paw model 1a: The roman numerals represent those animals treated with various doses of rh Mn-SOD with intraperitoneal (i.p.) route (KG=body weight) I=50 µg/kg KG, II=100 µg/kg KG, III=200 µg/kg KG, IV=400 µg/kg KG, V=800 µg/kg KG, VI=2 mg/kg KG. Each value shows the average data from 6 animals (after 4 hours and 24 hours) and is expressed as a percentage change compared with the placebo [phosphate buffer] (0%). *=p<0.05, =p<0.01, *=p<0.001 as significant differences from the placebo group (unpaired Student t-Test).

1b: The symbols represent the animals treated intraperitoneally (i.p.) with solvent [phosphate buffer] (□) or with Cu/Zn-SOD at a dosage of 100 µg/kg (■). Each dot shows the average data from six animals and the vertical bars indicate the standard deviation.

FIGS. 2a and 2b depict graphs showing the dosage reaction of (a) rh Mn-SOD and (b) Cu/Zn-SOD in joint oedemas in a carrageenan-induced synovitis model.

2a: The symbols represent the animals treated by intra-articular (i.a.) route with solvent [physiological NaCl-solution] (□), or rh Mn-SOD in a dosage of 5 µg (■), 12.5 µg (Δ), 25 µg (▲) or 50 µg (X). Each dot indicates the data averaged out from six or seven animals; the vertical bars indicate the standard deviation.

2b: The symbols represent the animals treated by intra-articular (i.a.) route with solvent [physiological NaCl-solution] (□), or Cu/Zn-SOD at a dosage of 5 µg (■), or 50 µg (X). Each dot indicates the data averaged out from five or six animals; the vertical bars indicate the standard deviation. *=p<0.05, =p<0.01, *=p<0.001, as significant differences from the animals injected with solvent (unpaired Student T-test).

DESCRIPTION OF THE PREFERRED EMBODIMENT

Surprisingly, it has been found that the use of Mn-SOD in a low dosage range of from 1 to 200 µg/kg of body weight as a daily dose was highly effective in treating and preventing diseases caused by oxygen free radicals, and that only in this dosage range was a cell or cytoprotective activity achieved without any harmful effects. The preferred dosage range is from 1 to 100 µg/kg of body weight, particularly from 1 to 50 µg/kg of body weight, these dosages referring to a daily dose. In inflammatory diseases which affect the joints directly, e.g. arthritic processes and synovial inflammatory processes, (synovitis), doses of 1 to 20 µg, more particularly 1 to 10 µg and most particularly 1 to 5 µg of Mn-SOD, based on the volume of a knee joint of a rat, have proved very effective. The knee joint of an adult rat (of approximately 200 g) has a volume of 100 µl on average (Miao, F. J.-P., et al., *J. Pharm. Exp. Ther.* 262:889–895 (1992); Vadas, P., et al., *Am. J. Pathol.* 134:807–811 (1989)).

The efficacy of the low dose of Mn-SOD according to the invention was highly significant in animal trials and there is no doubt that this low dosage can also be used to prepare a pharmaceutical preparation for the therapeutic or prophylactic treatment of diseases, especially inflammation, or conditions caused by oxygen free radicals in humans.

Surprisingly, it has also been found that Mn-SOD in the dosage according to the invention, is very much more effective than Cu/Zn-SOD and that high doses of Mn-SOD (>200 µg/kg or >25 µg/100 µl of joint volume) and Zn/Cu-SOD in general (100 µg/kg or 5 to 50 µg/100 µl of joint volume) either resulted in an exacerbation of the disease processes or were ineffective.

From the exacerbation of cell or tissue damage found at high Mn-SOD doses of above 200 µg/kg or above 25 to 50 µg/100 µl of joint volume in joint inflammation such as arthritic diseases (e.g. synovitis), it can only be assumed that these harmful effects might be caused by an increased formation of $H_2O_2$ as a result of the disproportion reactions of Mn-SOD, whilst hydroxyl radicals might be formed by interactions with reduced transition metals (e.g. Fe, Mn). Hydroxyl radicals of this kind are highly reactive and might rapidly combine with various molecules at the site where they are produced. It is also possible for oxygen radicals to react with nitric oxide (NO) to form peroxynitrite ($NO_3^-$), which results in the formation of hydroxyl radicals through the reaction ($NO_3^- + H^+ \rightarrow NO_3H$) and, according to the subsequent reaction, $NO_3H \rightarrow OH + NO_2$. The prolonged vasorelaxant effects of NO caused by overscavenging of $O_2^-$ by Mn-SOD could lead to extravasation and oedema, which could be responsible for the inflammatory effects, and which were found in the investigations shown here with high doses of Mn-SOD (>200 µg/kg or >25–50 µg/100 µl of joint volume). It is also possible that Mn-SOD participates in the reversible reduction of NO into the nitroxyl anion.

With regard to the diseases and conditions to be treated by the dosage according to the invention, which are caused, partly caused or triggered by oxygen free radicals or in which oxygen free radicals display undesirable properties, these include for example all kinds of inflammatory processes (such as for example synovial inflammation, Crohn's disease, colitis, rheumatic processes), tissue damage caused by medical intervention (e.g. reperfusion with subsequent ischaemia) or as a result of mechanical, physical (e.g. radiation) or chemical effects, organ and tissue transplants or arthritic processes. In particular, the inflammations include such processes which are peracute, acute, subacute, chronic or recurring as well as those known as localized, generalized or metastizing inflammations regarding their extent and location. These include all kinds of known exudative granulomatous and proliferative inflammations.

The Mn-SOD to be used in the low dosage according to the invention, can preferably be prepared by the known methods of DNA recombination, the process according to EP-A 282 899 being preferred. See also, EP-A 284 105. Preferably, the Mn-SOD is human.

The Mn-SOD to be used according to the invention may occur in all the formations familiar to those skilled in the art, be they parenteral or enteral or for systemic or topical use, although systemic application is preferred (e.g. i.v., i.m., s.c., i.a., i.p.). The sustained release forms and/or microencapsulated forms (e.g. in liposomes) known to those skilled in the art may well be used for the purposes according to the invention. See, Remington's *Pharmaceutical Sciences*, 18th Edition, Mack Publishing Co., Easton, Pa., Osol (ed.) (1990).

In order to prepare the particular preparations, pharmaceutically acceptable excipients and carriers known in the art are used, e.g. NaCl, Na-phosphate, hydroxypropyl-β-cyclodextrin (HPBCD), mannitol and hydroxyethylcellulose. Methods for preparing and administering such pharmaceutical compositions are taught in Remington's *Pharmaceutical Sciences*, 18th Edition, Mack Publishing Co., Easton, Pa., Osol (ed.) (1990).

For systemic treatment, Mn-SOD, preferably the recombinant Mn-SOD, according to EP-A 282 899, may be administered either as a bolus or in a single dose at the dosage according to the invention, to or into the diseased tissue (i.m., s.c., i.p.) or into the bloodstream by some other way (i.v., i.a.) or by infusion, whilst the preparation may be given once or several times a day or on successive days, weekly or monthly depending on the nature, severity and response rate of the disease.

It is intended that any mammal may be treated with the pharmaceutical compositions of the present invention. Preferably, such a mammal is a human, however, the invention is not intended to be so limited. Any mammal which may benefit from therapeutic treatment with the pharmaceutical compositions of the present invention are intended to be within the scope of the present invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. All the results are shown as an average +standard errors of the average values (standard deviation). Significance analysis was calculated according to the unpaired Student T-test. A probability of 0.05 was established as the minimum significance level.

EXAMPLE 1

Adjuvant-induced oedema in the rat paw

Paw oedemas were induced in groups of six male wistar rats (150 to 200 g) by a single subplantare injection (50 µl) of Freund's Complete Adjuvant (FCA, heat-inactivated mycobacterium tuberculosis, human strains, C, DT and PN mixed together [Central Veterinary Laboratories, MAFF, Weybridge, Surrey, U.K., freeze-dried] suspended in liquid paraffin BP/10 mg/ml). The rats had been immunized six days earlier with 75 µl FCA, administered to the back of the neck. Human recombinant manganese superoxide dismutase (rh Mn-SOD) with a specific activity of 3625 U/mg of protein (prepared according to EP-A 282 899 and obtained from Bender & Co. GesmbH, Vienna) was dissolved in phosphate buffer (0.06M, pH 7.8) in final concentrations of 50, 100, 200, 400, 800 µg/kg and 2 mg/kg and administered one hour before the FCA induction into a paw in one group of rats (n=6) by intraperitoneal route.

An additional group of rats (n=6) were given Cu/Zn-SOD (from human erythrocytes, specific activity 3610 U/mg Protein, Sigma Chemical Company, U.K.), dissolved in phosphate buffer as described above (100 µg/kg o of body weight) one hour before the FCA induction. The paw oedemas were assessed by measuring the circumference of the paw (in mm) 4 hours and 24 hours after FCA induction and the results were expressed as a difference in size between the inoculated paw and uninoculated paw.

Figure 1B:
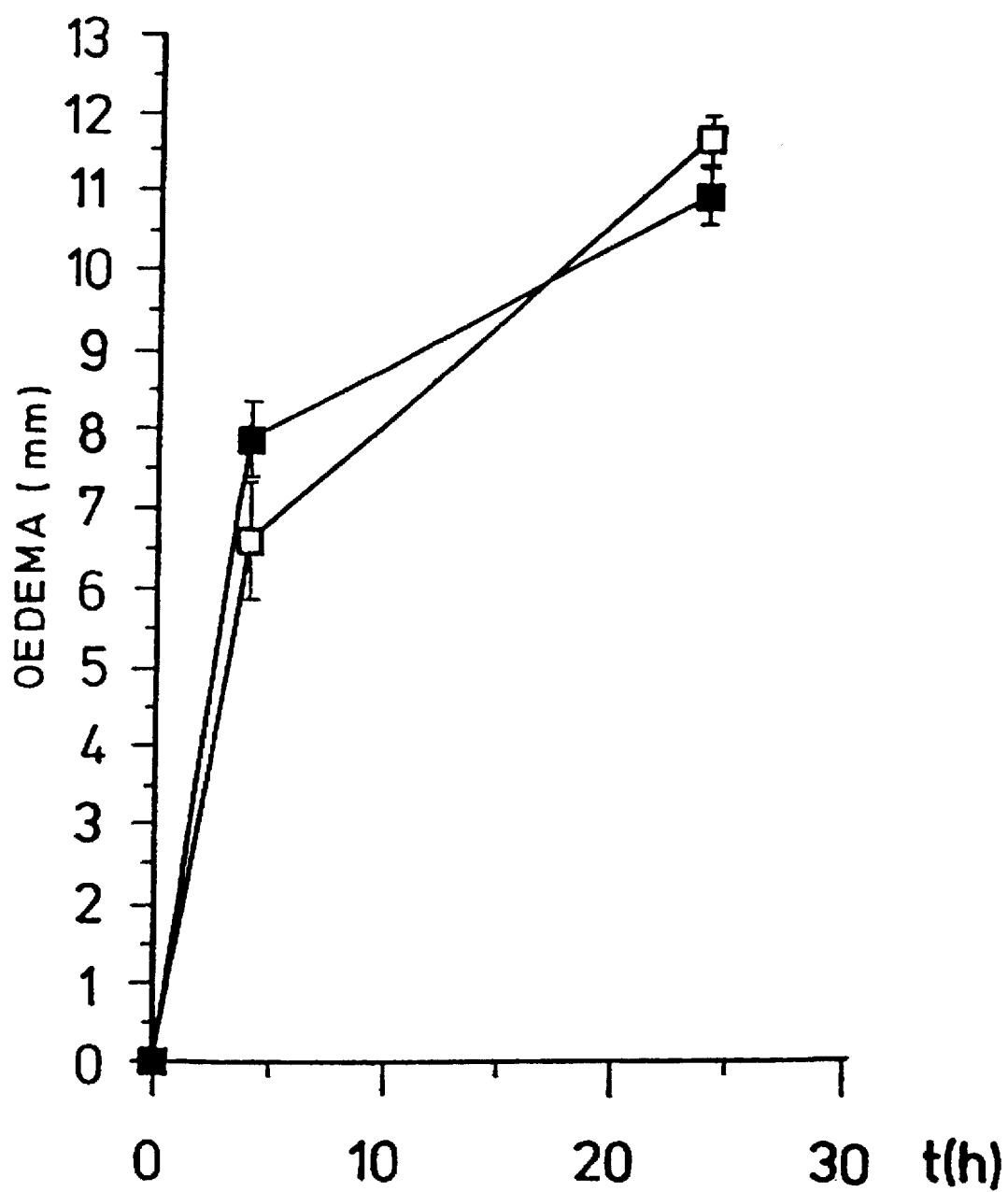

Using this model of a cell-mediated hypersensitivity reaction as an example, the dosage-reaction effect of rh Mn-SOD was investigated in oedemas which developed 4 hours and 24 hours after FCA induction. After FCA induction, the paw oedemas developed rapidly within the first 4 hours and reached their maximum after 24 hours. FIG. 1a shows the complete series of experiments carried out, in which the effects of rh Mn-SOD were calculated as a percentage change from the placebo. Pre-treatment with rh Mn-SOD resulted in a "parabolic" dosage-reaction effect, in which higher rh Mn-SOD doses (400–800 µg/kg and 2 mg/kg) had a pro-inflammatory reaction both after 4 hours and also to a lesser extent after 24 hours. A significant reduction in oedema was detected at the lower dosage range of rh Mn-SOD (50, 100, 200 µg/kg) with average reduction values after 4 hours of 43% ($p<0.001$) or 25% ($p<0.01$) and 43% ($p<0.001$) and 19% ($p<0.001$) at the two lower rh Mn-SOD doses (50, 100 µg/kg after 24 hours). In the groups treated with Cu/Zn-SOD, no significant change could be detected in the development of the oedemas (FIG. 1b).

EXAMPLE 2

Carrageenan-induced synovitis model in the rat

An inflammation was induced in the knee joint of groups of six to seven male wistar rats (150 to 200 g) by a single intra-articular injection (50 µl) of carrageenan (1% w/v in sterile physiological saline solution; carrageenan viscarin 402 made by Marine Colloids Inc., Springfield, USA). At specific times after induction (0, 4, 24, 48 hours) the joint oedemas were assessed by measurement of the width of the knee (mm) and were expressed as the difference between the injected knee joint and the contralateral non-injected knee joint. Groups of rats (n=6–7) were given a single intra-articular injection (50 µl), into one knee joint, of either a) carrageenan, b) carrageenan rh Mn-SOD (5, 12.5, 25, 50 µg; activity, solution and origin of the rh Mn-SOD as specified in Example 1), c) rh Mn-SOD (50 µg), d) carrageenan+Cu/Zn-SOD (5.50 µg; activity, solution and origin of Cu/Zn-SOD as specified under Example 1) or e) saline (physiological saline solution).

The intra-articular (i.a.) injection (50 µl) of 1% w/v carrageenan into a knee joint in rats resulted in a uniform increase in the joint oedemas which reached its maximum after 24 hours. Treatment with rh Mn-SOD in doses of 25 and 50 µg (i.a.) resulted in marked exacerbation of the oedema reaction up to 48 hours after induction (FIG. 2a). A significant reduction in oedema formation (44%, $p<0.05$) was only achieved with the lower dose of rh Mn-SOD (5 µg) at the 24 hour stage. There were no unfavorable effects on the circumference of the joint after the administration of either rh Mn-SOD (50 µg) or saline on its own.

However, in the group treated with Cu/Zn-SOD up to 48 hours after injection, a significant pro-inflammatory effect was observed.

EXAMPLE 3

Mn-SOD formulations

The following solutions are suitable for the use according to the invention of Mn-SOD, e.g. for i.v., i.m., s.c., i.a., i.p., enema and topical applications:

1. MnSOD 0.1–20 mg/ml
   NaCl 150 mM
   Na-Phosph. 10 mM
   pH 5.8–7.5
2. MnSOD 0.1–20 mg/ml
   HPBCD 6%
   Na-Phosph. 10 mM
   pH 5.8–7.5

The following formulation is particularly suitable for enemas or topical use:

3. MnSOD (0.15–3 mg/ml) in hydrogel (1.75% hydroxyethylcellulose, 0.2% methylparaben as preservatives).

From the foregoing description, one skilled in the art can easily ascertain the essential characteristics of this invention, and without departing from the spirit and scope thereof, can make various changes and modifications of the invention to adapt it to various usages and conditions, without undue experimentation. All patents and publications cited herein are fully incorporated by reference herein in there entirety.

What is claimed is:

1. A method for treating inflammation in a mammal in need of such treatment, comprising administering to said mammal 1 to 200 µg of Mn-SOD/per kg of body weight of said mammal/per day, as an active ingredient, in association with one or more pharmaceutically acceptable carriers or excipients, wherein said administering is by a route selected from the group consisting of intravenous and intraperitoneal administration.

2. The method according to claim 1, wherein the pharmaceutical composition contains 1 to 100 µg/kg of body weight of Mn-SOD.

3. The method according to claim 1, wherein the preparation contains 1 to 50 µg/kg of body weight of Mn-SOD.

4. A method for the therapeutic or prophylactic treatment of inflammation in the joint of a mammal, comprising administering intra-articularly to a mammal in need of such treatment a pharmaceutical composition containing 1 to 20 µg of Mn-SOD, per 100 µl of synovial fluid present in the joint.

5. The method according to claim 4, wherein the pharmaceutical composition contains 1 to 10 µg of Mn-SOD.

6. The method according to claim 5, wherein the pharmaceutical composition contains 1 to 5 µg of Mn-SOD.

7. The method according claim 1, wherein said pharmaceutical composition is administered by intravenous administration.

* * * * *